(12) United States Patent
Fitzgerald

(10) Patent No.: US 7,291,134 B2
(45) Date of Patent: Nov. 6, 2007

(54) MEDICAL CONNECTOR

(75) Inventor: Lisa M. Fitzgerald, Sarasota, FL (US)

(73) Assignee: P. Rowan Smith, Jr., Houston, TX (US)

( * ) Notice: Subject to any disclaimer, the term of this patent is extended or adjusted under 35 U.S.C. 154(b) by 243 days.

(21) Appl. No.: 10/971,906

(22) Filed: Oct. 25, 2004

(65) Prior Publication Data

US 2006/0089605 A1   Apr. 27, 2006

(51) Int. Cl.
*A61M 25/00* (2006.01)

(52) U.S. Cl. ...................... 604/247; 604/284

(58) Field of Classification Search .. 604/99.01–99.04, 604/167.03, 236, 237, 320, 323, 537, 249, 604/284, 247, 256, 246
See application file for complete search history.

(56) References Cited

U.S. PATENT DOCUMENTS

| | | | |
|---|---|---|---|
| 3,572,375 A | * | 3/1971 | Rosenberg ................. 137/512 |
| 3,601,152 A | * | 8/1971 | Kenworthy ................. 137/843 |
| 4,683,916 A | | 8/1987 | Raines |
| 4,986,310 A | * | 1/1991 | Bailey et al. ............... 137/859 |
| 5,176,658 A | * | 1/1993 | Ranford ...................... 604/247 |
| 5,401,245 A | * | 3/1995 | Haining ....................... 604/86 |
| 5,441,487 A | | 8/1995 | Vedder |
| 5,533,983 A | | 7/1996 | Haining |
| 5,848,605 A | * | 12/1998 | Bailey et al. ............... 137/540 |
| 5,992,462 A | * | 11/1999 | Atkinson et al. .......... 137/854 |

* cited by examiner

*Primary Examiner*—Nicholas Lucchesi
*Assistant Examiner*—Theodore J. Stigell
(74) *Attorney, Agent, or Firm*—Richard L. Moseley

(57) ABSTRACT

A needleless connector for adding medication to a parenteral fluid is provided. The needleless connector comprises a connector adapted to receive a syringe and having a check valve to seal the port in place of a puncture pad. The check valve comprises a resilient disc held in place and biased closed by the tensile stress of the check valve material. When a syringe or other apparatus having a male luer connector is engaged with the connector and fluid pressure is applied to the check valve the resilient disc is deformed which allows the medication to flow through the connector into the tubing and thus to the patient.

2 Claims, 4 Drawing Sheets

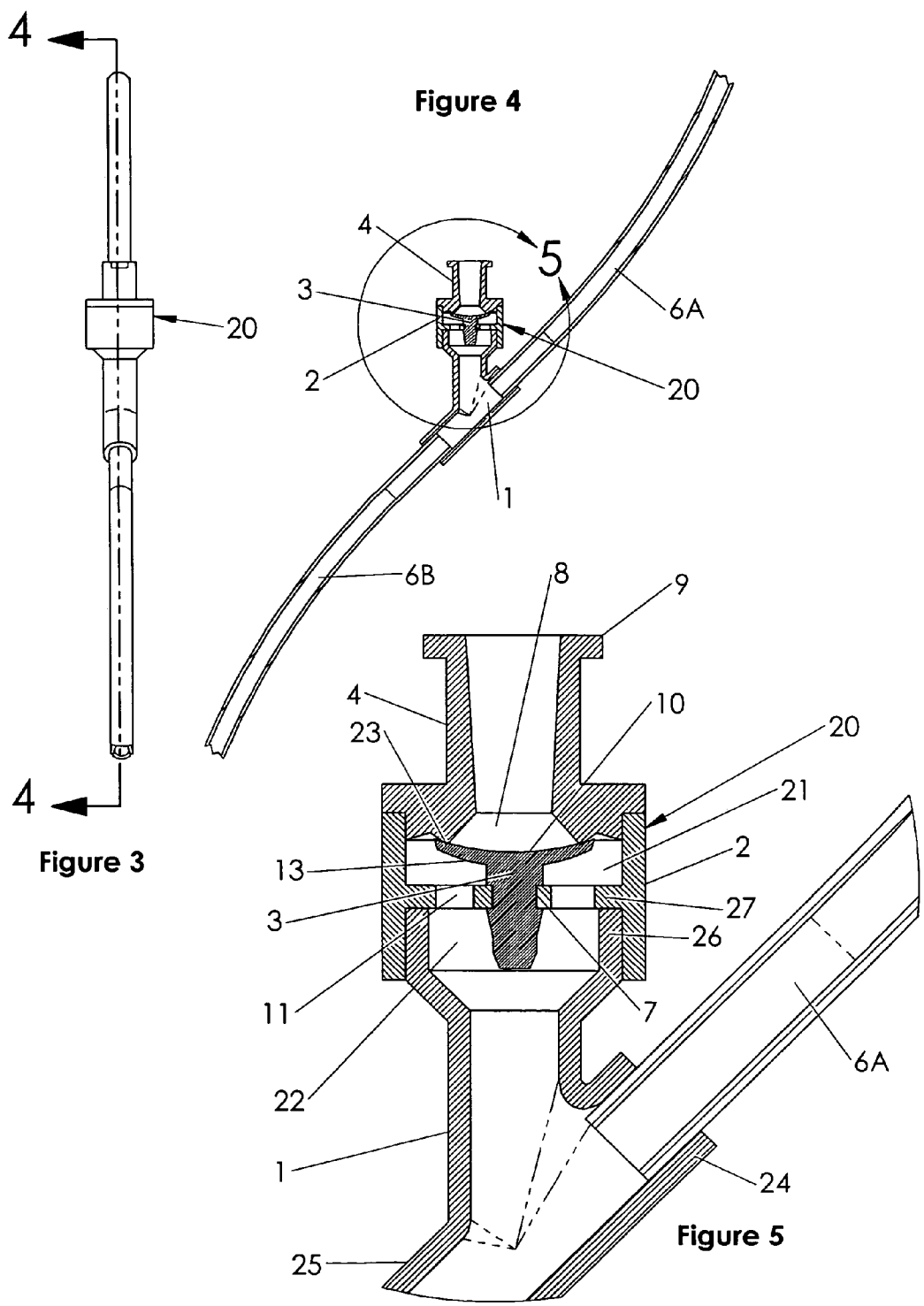

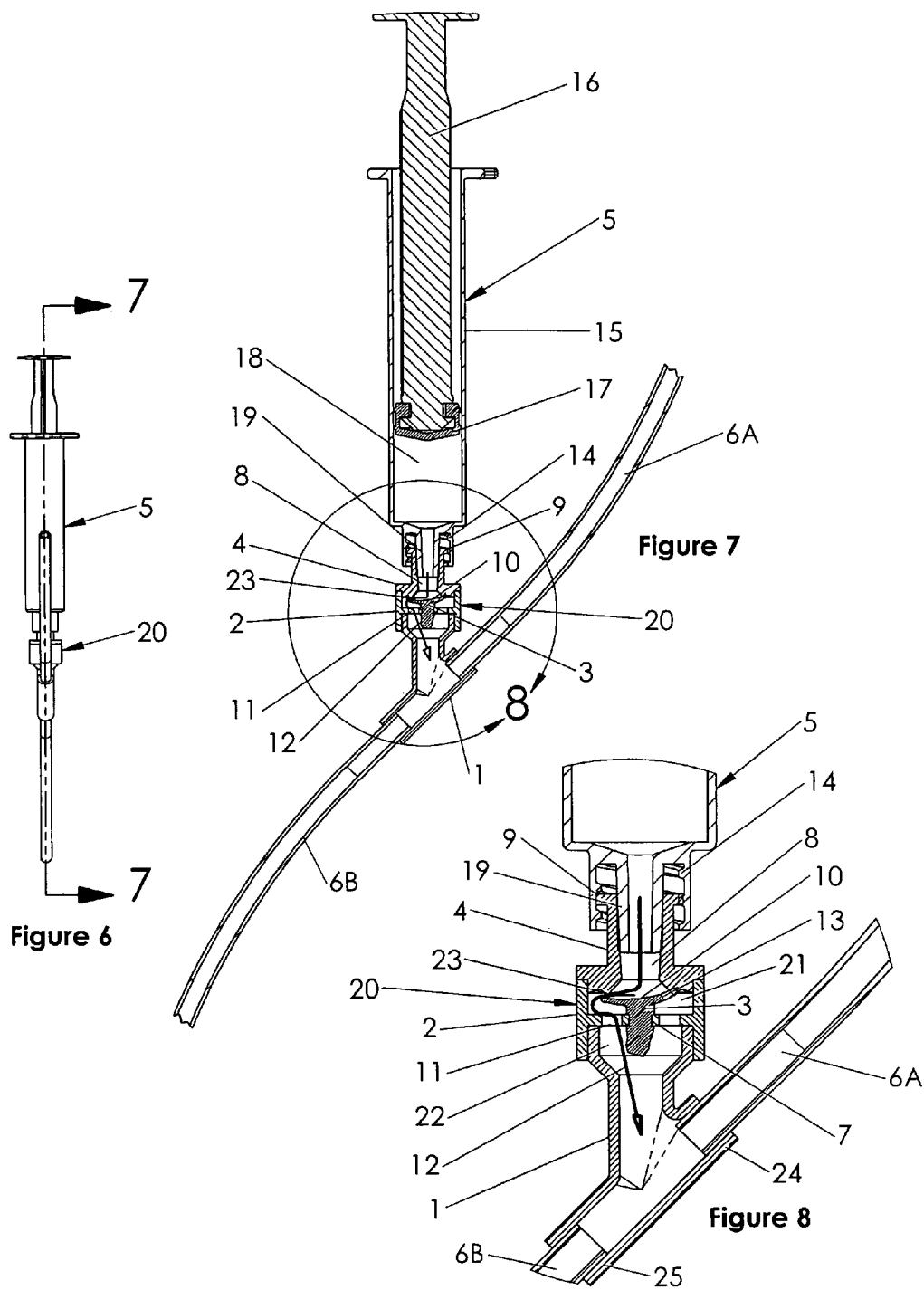

MEDICAL CONNECTOR

BACKGROUND OF THE INVENTION

1. Field of the Invention

This invention relates to medical connectors used in the introduction of liquids into patients via intravenous solutions. More particularly the invention relates to a needleless connection for use with syringes or other apparatus having a standard luer lock type connection.

2. Related Information

It is a common practice in treating patients, particularly patients who must be cared for under emergency conditions, using medications introduced into the patient intravenously. An intravenous solution, commonly referred to as parenteral fluid, is fed from a container or I.V. bag through a tubing and a catheter which has been inserted into the patient's vein. The catheter is secured to the patient by a strip of adhesive tape. The medication to be administered is generally added to the parenteral fluid through a Y connector in the tubing. The conventional practice has been to inject the fluid using a hypodermic syringe and needle through a sealed entry port in Y connector in the tubing. Generally the seal at the port is a puncture pad of generic latex which for a limited number of uses will reseal itself when a needle is withdrawn.

One problem with this conventional practice is that the needle may be pulled loose from the sealed port very easily. Another problem is needle sticks. From time to time a nurse in attempting to insert the needle into the port will accidentally stick himself or herself with the needle. While there is little risk of infection to the nurse if the needle is new and sterile, the process may be slowed until the needle has been replaced. Lopez, et al in U.S. Pat. No. 4,752,292 have presented one solution to the problem.

The connector of Lopez, et al presumes that the needle connector may be easily attached to the source of medication. When measured doses are necessary syringes are more often used and the Lopez connector is not practical.

Another solution has been presented by Haining in U.S. Pat. No. 5,785,693 wherein a spring actuated valve is placed in a Y connector on the I.V. tube. While useful, the valve of Haining has several moving parts, such as the valve stem and spring, which may foul. In addition the materials of construction, especially of the spring, have to be medical grade material.

It is an object of the present invention to provide a needleless connector having a simplified valve for administering medication through a Y connector of an I.V. system.

SUMMARY OF THE INVENTION

In its simplest form the present invention comprises a connector adapted to receive a syringe and having a check valve to seal the port in place of a puncture pad. The check valve comprises a resilient disc held in place and biased closed by the tensile stress of the check valve material. When a syringe or other apparatus having a male luer connector is engaged with the connector and fluid pressure is applied to the check valve the resilient disc is deformed which allows the medication to flow through the connector into the tubing and thus to the patient. The invention may be described as a connector for adding a fluid to a intravenous solution, comprising:

(a) a cylindrical body having an upper cavity and a lower cavity, said upper cavity having a valve seat at the upper end;

(b) a valve stem securely mounted between said cavities;

(c) a resilient disc mounted on said stem and biased against said seat;

(d) said resilient disc being displaced from said seat by the force of fluid passing through said first port into said body.

BRIEF DESCRIPTION OF THE DRAWING

FIG. 3 is a side plan view of the connector of the present invention.

FIG. 4 is a plan view in cross section taken along lines 4-4 of FIG. 3.

FIG. 5 is an enlarged view of the area circled in FIG. 4.

FIG. 6 is a side plan view of the connector of the present invention having a syringe attached.

FIG. 7 is a plan view in cross section taken along lines 7-7 of FIG. 6.

FIG. 8 is an enlarged view of the area circled in FIG. 7.

DESCRIPTION OF THE PREFERRED EMBODIMENT

For a detailed description of the preferred embodiment the reader is directed to the accompanying figures in which like components are given like numerals for ease of reference.

Figure 1:
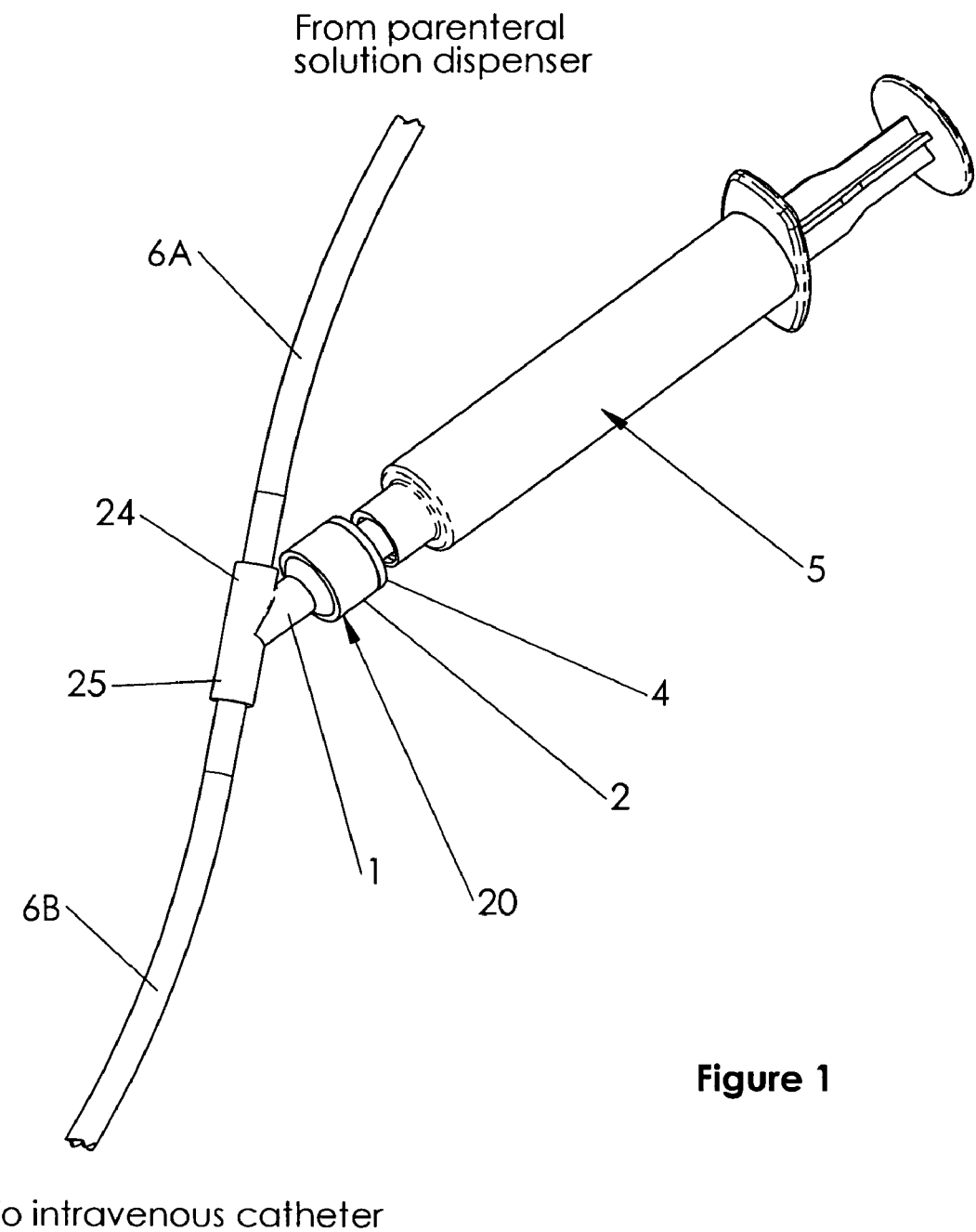
FIG. 1 is a schematic view of a conventional I.V. system and an adapter connector of the present invention and a syringe.
Figure 2:
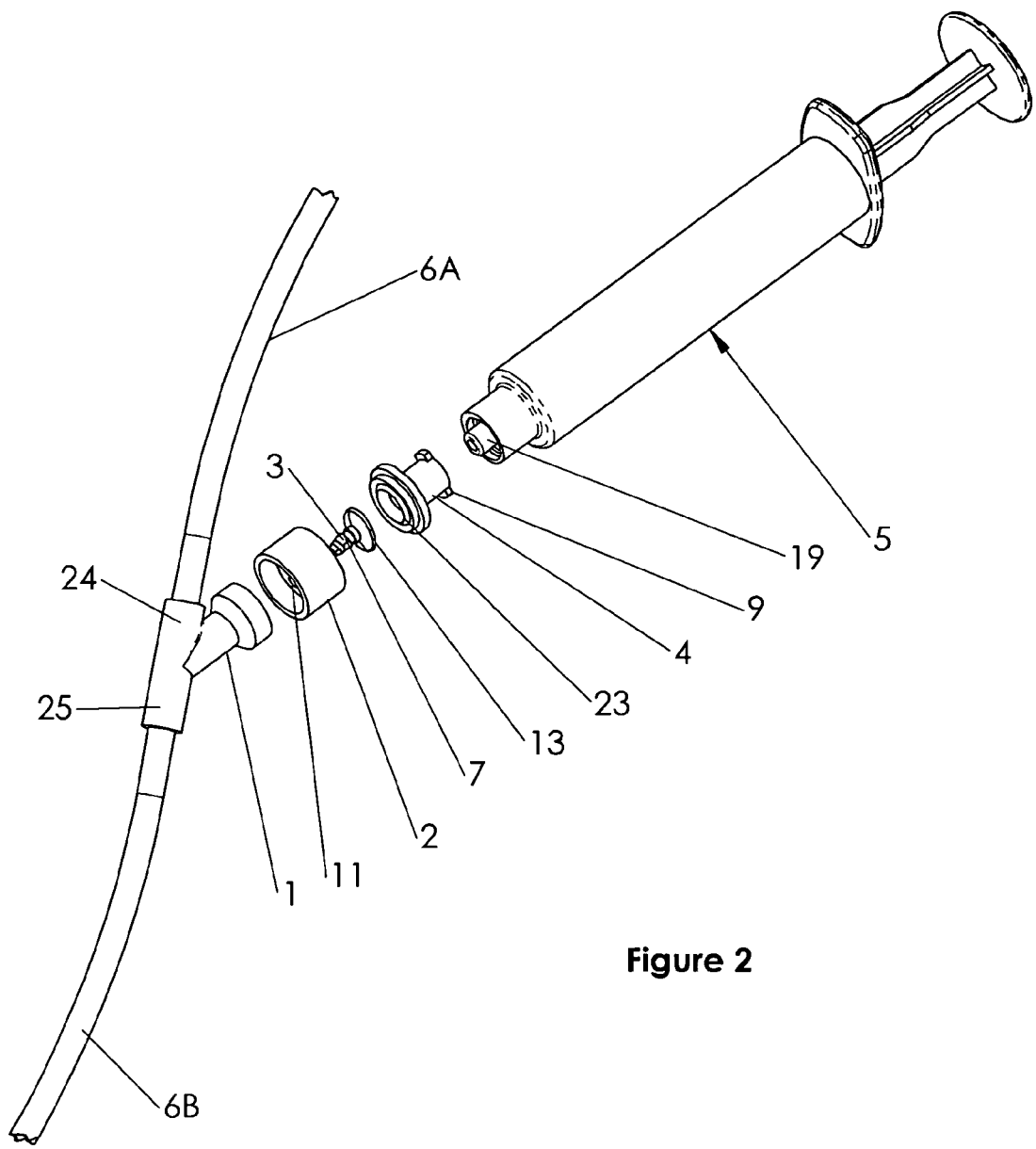
FIG. 2 is an exploded view of FIG. 1.

Referring first to FIG. 1 there is shown an intravenous fluid administration system. A first tube 6A is attached by one end to a source of parenteral solution (not shown) and by the opposite end to a Y connector 1. A second tube 6B is connected at a first end to the lower end of the Y connector and at the lower end is connected to an intravenous catheter (not shown). Since the fluid is administrated by gravity flow the direction up, down, upper and lower have definite meanings.

The Y connector is shown to have three connection points or ports. The first port 20 is for receiving the medication which is injected from a syringe 5 and should be angled up from the horizontal to allow injected fluid to flow by gravity into the Y connector and tube 6B. The second port 25 is connected to the end of catheter tube 6B. The third connection port 24 is for connection to the parenteral fluid tube 6A. The first port 2 extends at an angle from the Y connector 1 such that it is less than 90° from the vertical or from the third port 24.

A puncture pad normally provides for a resealable access to the Y connector. To replace the function of the puncture pad a valve is provided within the connector 1, the details of which are shown in FIGS. 2-8.

Referring now to FIGS. 3-8 the construction of the port 20 containing the valve is shown. The valve includes a cylindrical housing 2 which fits snugly onto Y connector 1 at 26 and is secured there by an appropriate cement. The valve is divided into upper cavity 21 and lower cavity 22 by spider 27 having flow opening 11. Near the opening of upper cavity 21 is a valve seat 23. A valve stem 3 is securely mounted in spider 27 and held in place by retaining notch 7. Stem 3 extends into either cavity 21 and 22. At the upper end of stem 3 is a resilient disc 13 having a face 10 which contacts seat 23 to seal the valve. The upper end of the port includes a barrel 4 which defines a valve volume 8 and has male luer connector 9 on the upper extremity.

Referring now to FIGS. 6-8 the syringe 5 is shown connected to the port 20 of Y connector 1. Syringe 5 includes barrel 15 which defines fluid chamber 18. Plunger 16 is located in barrel 15 and includes plunger seal 17. Threads 14 in syringe engage the luer connection 9 on upper end of barrel and luer extension 19 on syringe is forced downward to substantially fill valve volume 8. This allows for maximum transfer of fluid with minimum residual in the access port 20. As plunger 15 is depressed fluid is forced from the fluid chamber 18 into the valve and the resilient disc 13 is deformed away from seat 23 and fluid is allowed to follow flow path 12. The flow of fluid may be followed by the arrows. When fluid flow is stopped any back pressure will force the resilient disc 13 back against seat 23 and seal the connection.

The foregoing description of the invention has been directed to a particular preferred embodiment of the present invention for the purposes of explanation and illustration. It will be apparent to those skilled in the art that many modifications and changes in the apparatus may be made without departing from the scope and spirit of the invention. It is therefore intended that the following claims cover all equivalent modifications and variations as fall within the scope of the invention as defined by the claims.

The invention claimed is:

1. A connector for adding medication from a syringe to an intravenous fluid comprising:
   (a) a hollow cylindrical body having
      (i) a first port on one end for adding medication to the intravenous fluid,
      (ii) a second port on another end for connection to a catheter which is inserted into the vein of a patient, and
      (iii) a third port intermediate said first and second ports for attachment to a intravenous fluid source;
   (b) a luer connection on an open end of said first port;
   (c) a valve housing secured within said first port and having a spider dividing said housing into an upper cavity and a lower cavity and a valve seat on an underside of an upper end of said upper cavity opposite said spider;
   (d) a valve stem having a notch near the middle and mounted within said housing by the engagement of said notch with said spider;
   (e) a resilient disc mounted on said stem and biased against said seat;
   (f) said resilient disc being displaced from said seat by the force of fluid passing through said first port into said body.

2. A connector for adding medication from a syringe to an intravenous fluid comprising:
   (a) a hollow cylindrical body having
      (i) a first port on one end for adding medication to the intravenous fluid,
      (ii) a second port on another end for connection to a catheter which is inserted into the vein of a patient, and
      (iii) a third port intermediate said first and second ports for attachment to a intravenous fluid source;
   (b) a luer connection on an open end of said first port;
   (c) a valve housing secured within said first port, said valve housing being divided into an upper cavity and a lower cavity by a spider;
   (d) a valve seat on an underside at an upper end of said upper cavity opposite said spider;
   (e) a valve stem having a notch near the middle and securely mounted between said cavities by the engagement of said notch with said spider;
   (f) a resilient disc mounted on said stem and biased against said seat;
   (g) said resilient disc being displaced from said seat by the force of fluid passing through said first port into said body.

\* \* \* \* \*